United States Patent
Hermann

(10) Patent No.: US 7,256,021 B2
(45) Date of Patent: Aug. 14, 2007

(54) ENTEROBACTERIACEAE STRAINS WITH AN ATTENUATED ASPA GENE FOR THE FERMENTATIVE PRODUCTION OF AMINO ACIDS

(75) Inventor: Thomas Hermann, Bielefeld (DE)

(73) Assignee: Degussa AG, Düsseldorf (DE)

( * ) Notice: Subject to any disclaimer, the term of this patent is extended or adjusted under 35 U.S.C. 154(b) by 430 days.

(21) Appl. No.: 10/416,364

(22) PCT Filed: Jul. 3, 2002

(86) PCT No.: PCT/EP02/07351

§ 371 (c)(1),
(2), (4) Date: May 12, 2003

(87) PCT Pub. No.: WO03/008603

PCT Pub. Date: Jan. 30, 2003

(65) Prior Publication Data

US 2004/0115780 A1 Jun. 17, 2004

Related U.S. Application Data

(60) Provisional application No. 60/306,867, filed on Jul. 23, 2001.

(30) Foreign Application Priority Data

Jul. 18, 2001 (DE) ................ 101 35 051

(51) Int. Cl.
*C12P 13/08* (2006.01)
*C12N 1/21* (2006.01)
*C12N 15/00* (2006.01)
*C12N 15/70* (2006.01)
*C12Q 1/68* (2006.01)

(52) U.S. Cl. ............... 435/115; 435/6; 435/252.33; 435/320.1; 435/488

(58) Field of Classification Search .......... 435/115, 435/252.3, 320.1
See application file for complete search history.

(56) References Cited

U.S. PATENT DOCUMENTS 3,647,628 A * 3/1972 Nakayama et al. ........ 435/115

(Continued)

FOREIGN PATENT DOCUMENTS

EP 0 994 190 A2 4/2000

(Continued)

OTHER PUBLICATIONS

Menkel et al. Influence of increased aspartate availability on lysine formation by a recombinant strain of *Corynebacterium glutamicum* and utilization of fumarate, Appl Environ Microbiol. Mar. 1989; 55 (3): 684-8.*

(Continued)

*Primary Examiner*—Manjunath N. Rao
*Assistant Examiner*—Iqbal Chowdhury
(74) *Attorney, Agent, or Firm*—Michael A. Sanzo; Law Office of Michael A. Sanzo, LLC

(57) ABSTRACT

The invention relates to a process for the preparation of L-amino acids, especially L-lysine, L-valine, L-homoserine and L-threonine, by fermenting a microorganism of the genus *Escherichia* which has a mutation or deletion in the gene encoding aspartate ammonium lyase (aspA). This mutation results in the loss of aspA enzymatic activity in the microorganism

11 Claims, 1 Drawing Sheet

U.S. PATENT DOCUMENTS

| | | | | |
|---|---|---|---|---|
| 4,278,765 | A | 7/1981 | Debabov et al. | 435/172 |
| 4,347,318 | A | 8/1982 | Miwa et al. | 435/115 |
| 6,197,590 | B1 * | 3/2001 | Richaud et al. | 435/473 |
| 7,011,961 | B2 * | 3/2006 | Noh et al. | 435/115 |

FOREIGN PATENT DOCUMENTS

| | | |
|---|---|---|
| EP | 1 013 765 A1 | 6/2000 |
| WO | WO99/18228 | 4/1999 |
| WO | WO 01/05939 A1 | 1/2001 |
| WO | WO 01/92545 A1 | 12/2001 |
| WO | WO 02/06459 A1 | 1/2002 |
| WO | WO 03/008600 A2 | 1/2003 |
| WO | WO 03/008602 A2 | 1/2003 |
| WO | WO 03/008604 A2 | 1/2003 |
| WO | WO 03/008616 A2 | 1/2003 |

OTHER PUBLICATIONS

Alefounder, et al., "Cloning, Sequence Analysis and Over-expression of the gene for the Class II Fructose 1,6-Bisphosphate Aldolase of *Escherichia coli*," *Biochem. J. 257*:529-534 (1989).

Blattner, et al., "The Complete Genome Sequence of *Escherichia coli* K-12," *Science 277*:1453-1462 (1997).

Byrne, et al., "DNA Sequences of the *cysK* Regions of *Salmonella typhimurium* and *Escherichia coli* Linkage of the *cysK* Regions to *ptsH*," *J. Bacteriol. 170*:3150-3157 (1988).

Byrne, et al., "Nucleotide Sequence of the *aceB* Gene Encoding Malate Synthase A in *Escherichia coli*," *Nucleic Acids Res. 16*:9342-(1988).

Chandrasekhar, et al., "Purification and Properties of the groES Morphogenetic Protein of *Escherichia coli*," *J. Biol. Chem. 261*:12414-12419 (1986).

Chao, et al., "Selective Production of L-aspartic Acid and L-phenylalanine by Coupling Reactions of Aspartase and Aminotransferase in *Escherichia coli*," *Enzyme and Microbial Tech. 27*:19-25 (2000).

Clarke, et al., "Nucleotide Sequence of the *pntA* and *pntB* Genes Encoding the Pyridine Nucleotide Transhydrogenase of *Escherichia coli*," *Eur. J. Biochem. 158*:647-653 (1986).

Cortay, et al., "Nucleotide Sequence and Expression of the *aceK* Gene Coding for Isocitrate Dehydrogenase Kinase/Phosphatase in *Escherichia coli*," *J. Bacteriol. 170*:89-97 (1988).

Erni, et al., "Glucose-Permease of the Bacterial Phosphotransferase System," *J. Biol. Chem. 261*:16398-16403 (1986).

Falzone, et al., "L-Aspartase from *Escherichia coli*: Substrate Specificity and Role of Divalent Metal Ions," *Biochem. 27*:9089-9093 (1988).

Ferrante, et al., "Cloning of an Organic Solvent-Resistance Gene in *Escherichia coli*: The Unexpected Role of Alkylhydroperoxide Reductase," *Proc. Natl. Acad. Sci. USA 92*:7617-7621 (1995).

Grabau, et al., "Nucleotide Sequence and Deduced Amino Acid Sequence of *Escherichia coli* Pyruvate Oxidase, a Lipid-Activated Flavoprotein," *Nucleic Acids Res. 14*:5449-5461 (1986).

Hosono, et al., "Decreasing Accumulation of Acetate in a Rich Medium by *Escherichia coli* on Introduction of Genes in a Multicopy Plasmid," *Biosci. Biotech. Biochem. 59*:256-261 (1995).

Jahreis, et al., "Nucleotide Sequences of the *ilvH-fruR* Gene Region of *Escherichia coli* K12 and *Salmonella typhimurium* LT2," *Mol. Gen. Genet. 226*:332-336 (1991).

Jayasekera, et al., "Evaluation of Functionally Important Amino Acids in L-Aspartate Ammonia-Lyase from *Escherichia coli*," *Biochemistry 36*:9145-9150 (1997).

Landgraf, et al., "The Role of H-NS in One Carbon Metabolism," *Biochimie 76*:1063-1070 (1994).

Lu, et al., "Molecular Cloning and Characterization of the *pgm* Gene Encoding Phosphoglucomutase of *Escherichia coli*," *J. Bacteriol. 176*:5847-5851 (1994).

Matsuoka, et al., "Isolation, Hyperexpression, and Sequencing of the *aceA* Gene Encoding Isocitrate Lyase in *Escherichia coli*," *J. Bacteriol. 170*:4528-4536 (1988).

McPherson, et al., "Complete Nucleotide Sequence of the *Escherichia coli gdhA* Gene," *Nucleic Acids Res. 11*:5257-5267 (1983).

Medina, et al., "Sequence of the *pckA* Gene of *Escherichia coli* K-12: Relevance to Genetic and Allosteric Regulation and Homology of *E. coli* Phosphoenolpyruvate Carboxykinase with the Enzymes from *Trypanosoma brucei* and *Saccharomyces cerevisiae*," *J. Bacteriol. 172*:7151-7156 (1990).

Menkel, et al., "Influence of Increased Aspartate Availability on Lysine Formation by a Recombinant Strain of *Corynebacterium glutamicum* and Utilization of Fumarate," *Applied Environ. Microbiol. 55*:684-688 (1989).

Niersbach, et al., "Cloning and Nucleotide Sequence of the *Escherichia coli* K-12 *ppsA* Gene, Encoding PEP Synthase," *Mol. Gen. Genet. 231*:332-336 (1992).

Ostrowski, et al., "DNA Sequences of the *cysB* Regions of *Salmonella typhimurium* and *Escherichia coli*," *J. Biol. Chem. 262*:5999-6005 (1987).

Ostrowski, et al., "Characterization of the Flavoprotein Moieties of NADPH-Sulfite Reductase from *Salmonella typhimurium* and *Escherichia coli*," *J. Biol. Chem. 264*:15796-15808 (1989).

Overduin, et al., "Nucleotide Sequence of the *ugp* Genes of *Escherichia coli* K-12: Homology to the Maltose System," *Molec. Microbiol. 2*:767-775 (1988).

Pon, et al., "Identification, Cloning, Nucleotide Sequence and Chromosomal Map Location of *hns*, the Structural Gene for *Escherichia coli* DNA-Binding Protein H-NS," *Mol. Gen. Genet. 212*:199-202 (1988).

Ravnikar, et al., "Structural and Functional Analysis of a Cloned Segment of *Escherichia coli* DNA that Specifies Proteins of a $C_4$ Pathway of Serine Biosynthesis," *J. Bacteriol. 169*:4716-4721 (1987).

Sabe, et al., "Molecular Cloning of the Phosphoenolpyruvate Carboxylase Gene, *ppc*, of *Escherichia coli*," *Gene 31*:279-283 (1984).

Saffen, et al., "Sugar Transport by the Bacterial Phosphotransferase System," *J. Biol. Chem. 262*:16241-16253 (1987).

Takagi, et al., "Cloning and Nucleotide Sequence of the Aspartase Gene of *Escherichia coli*," *Nucleic Acids Res. 13*:2063-2075 (1985).

Valle, et al., "Nucleotide Sequence of the Promoter and Amino-Terminal Coding Region of the Glutamate Dehydrogenase Structural Gene of *Escherichia coli*," *Gene 23*:199-209 (1983).

Vipond, et al., "Defined Deletion Mutants Demonstrate that the Major Secreted Toxins Are Not Essential for the Virulence of *Aeromonas salmonicida*," *Infection and Immunity 66*:1990-1998 (1998).

Vogel, et al., "Cloning and Sequence of the *mdh* Structural Gene of *Escherichia coli* Coding for the Malate Dehydrogenase," *Arch. Microbiol. 149*:36-42 (1987).

Willins, et al., "Characterization of Lrp, an *Escherichia coli* Regulatory Protein That Mediates a Global Response to Leucine," *J. Biol. Chem. 266*:10768-10774 (1991).

Woods, et al., "Structural and Functional Relationships Between Fumarase and Aspartase," *Biochem. J. 237*:547-557 (1986).

Woods, et al., "Differential Roles of the *Escherichia coli* Fumarases and *fnr*-dependent Expression of Fumarase B and Aspartase," *FEMS Microbiol. Letters 48*:219-224 (1987).

English language abstract for WO 99/18228, reference B1 above.

English language abstract for WO 01/05939, reference B3 above.

* cited by examiner

ENTEROBACTERIACEAE STRAINS WITH AN ATTENUATED ASPA GENE FOR THE FERMENTATIVE PRODUCTION OF AMINO ACIDS

CROSS REFERENCE TO RELATED APPLCIATIONS

The present application represents U.S. national stage of international application PCT/EP02/07351, with an international filing date of Jul. 3, 2002, and which was published in English under PCT Article 21(2) on Jan. 30, 2003. The international application claims priority to U.S. provisional application 60/306,867, filed on Jul. 23, 2001 and to German application 101 35 051.1, filed on Jul. 23, 2001.

FIELD OF THE INVENTION

This invention relates to a process for the fermentative preparation of L-amino acids, in particular L-threonine, using strains of the Enterobacteriaceae family in which the aspA gene is attenuated.

PRIOR ART

L-Amino acids, in particular L-threonine, are used in human medicine and in the pharmaceuticals industry, in the foodstuffs industry and very particularly in animal nutrition.

It is known to prepare L-amino acids by fermentation of strains of Enterobacteriaceae, in particular *Escherichia coli* (*E. coli*) and *Serratia marcescens*. Because of their great importance, work is constantly being undertaken to improve the preparation processes. Improvements to the process can relate to fermentation measures, such as e.g. stirring and supply of oxygen, or the composition of the nutrient media, such as e.g. the sugar concentration during the fermentation, or the working up to the product form, by e.g. ion exchange chromatography, or the intrinsic output properties of the microorganism itself.

Methods of mutagenesis, selection and mutant selection are used to improve the output properties of these microorganisms. Strains which are resistant to antimetabolites, such as e.g. the threonine analogue α-amino-β-hydroxyvaleric acid (AHV), or are auxotrophic for metabolites of regulatory importance and produce L-amino acid, such as e.g. L-threonine, are obtained in this manner.

Methods of the recombinant DNA technique have also been employed for some years for improving the strain of strains of the Enterobacteriaceae family which produce L-amino acids, by amplifying individual amino acid biosynthesis genes and investigating the effect on the production.

OBJECT OF THE INVENTION

The object of the invention is to provide new measures for improved fermentative preparation of L-amino acids, in particular L-threonine.

SUMMARY OF THE INVENTION

The invention provides a process for the fermentative preparation of L-amino acids, in particular L-threonine, using microorganisms of the Enterobacteriaceae family which in particular already produce L-amino acids and in which the nucleotide sequence which codes for the aspA gene is attenuated.

DETAILED DESCRIPTION OF THE INVENTION

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Threonine is particularly preferred.

The term "attenuation" in this connection describes the reduction or elimination of the intracellular activity of one or more enzymes (proteins) in a microorganism which are coded by the corresponding DNA, for example by using a weak promoter or a gene or allele which codes for a corresponding enzyme with a low activity or inactivates the corresponding enzyme (protein) or gene, and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

The process comprises carrying out the following steps:
a) fermentation of microorganisms of the Enterobacteriaceae family in which the aspA gene is attenuated,
b) concentration of the corresponding L-amino acid in the medium or in the cells of the microorganisms of the Enterobacteriaceae family, and
c) isolation of the desired L-amino acid, constituents of the fermentation broth and/or the biomass in its entirety or portions (>0 to 100%) thereof optionally remaining in the product.

The microorganisms which the present invention provides can produce L-amino acids from glucose, sucrose, lactose, fructose, maltose, molasses, optionally starch, optionally cellulose or from glycerol and ethanol. They are representatives of the Enterobacteriaceae family chosen from the genera *Escherichia*, *Erwinia*, *Providencia* and *Serratia*. The genera *Escherichia* and *Serratia* are preferred. Of the genus *Escherichia* the species *Escherichia coli* and of the genus *Serratia* the species *Serratia marcescens* are to be mentioned in particular.

Suitable strains, which produce L-threonine in particular, of the genus *Escherichia*, in particular of the species *Escherichia coli*, are, for example
  *Escherichia coli* TF427
  *Escherichia coli* H4578
  *Escherichia coli* KY10935
  *Escherichia coli* VNIIgenetika MG442
  *Escherichia coli* VNIIgenetika M1
  *Escherichia coli* VNIIgenetika 472T23
  *Escherichia coli* BKIIM B-3996
  *Escherichia coli* kat 13
  *Escherichia coli* KCCM-10132

Suitable L-threonine-producing strains of the genus *Serratia*, in particular of the species *Serratia marcescens*, are, for example
  *Serratia marcescens* HNr21
  *Serratia marcescens* TLr156
  *Serratia marcescens* T2000

Strains from the Enterobacteriaceae family which produce L-threonine preferably have, inter alia, one or more genetic or phenotypic features chosen from the group consisting of: resistance to α-amino-β-hydroxyvaleric acid, resistance to thialysine, resistance to ethionine, resistance to α-ethylserine, resistance to diaminosuccinic acid, resistance to α-aminobutyric acid, resistance to orrelidin, resistance to rifampicin, resistance to valine analogues, such as, for example, valine hydroxamate, resistance to purine analogues, such as, for example, 6-dimethylaminopurine, a need for L-methionine, optionally a artial and compensable need for L-isoleucine, a need for eso-diaminopimelic acid, auxotrophy in respect of threonine-containing dipeptides, resistance to L-threonine, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, optionally an ability for sucrose utilization, enhancement of the threonine operon, enhancement of homoserine dehydrogenase I-aspartate kinase I, preferably of the feed back resistant form, enhancement of homoserine kinase, enhancement of threonine synthase, enhancement of aspartate kinase, optionally of the feed back resistant form, enhancement of aspartate semialdehyde dehydrogenase, enhancement of phosphoenol pyruvate carboxylase, optionally of the feed back resistant form, enhancement of phosphoenol pyruvate synthase, enhancement of transhydrogenase, enhancement of the RhtB gene product, enhancement of the RhtC gene product, enhancement of the YfiK gene product, enhancement of a pyruvate carboxylase, and attenuation of acetic acid formation.

It has been found that microorganisms of the Enterobacteriaceae family produce L-amino acids, in particular L-threonine, in an improved manner after attenuation, in particular elimination, of the aspA gene.

The nucleotide sequences of the genes of *Escherichia coli* belong to the prior art and can also be found in the genome sequence of *Escherichia coli* published by Blattner et al. (Science 277: 1453–1462 (1997)).

The aspA gene is described, inter alia, by the following data:
Description: Aspartate ammonium lyase (aspartase)
EC No.: 4.3.1.1
Reference: Takagi et al.; Nucleic Acids Research 13(6): 2063–2,074 (1985); Woods et al.; Biochemical Journal 237(2): 547–557 (1986); Falzone et al.; Biochemistry 27(26): 9089–9093 (1988); Jayasekera et al.; Biochemistry 36(30): 9145–9150 (1997)
Accession No.: AE000486

The nucleic acid sequences can be found in the databanks of the National Center for Biotechnology Information (NCBI) of the National Library of Medicine (Bethesda, Md., USA), the nucleotide sequence databank of the European Molecular Biologies Laboratories (EMBL, Heidelberg, Germany or Cambridge, UK) or the DNA databank of Japan (DDBJ, Mishima, Japan).

The genes described in the text references mentioned can be used according to the invention. Alleles of the genes which result from the degeneracy of the genetic code or due to "sense mutations" of neutral function can furthermore be used.

To achieve an attenuation, for example, expression of the gene or the catalytic properties of the enzyme proteins can be reduced or eliminated. The two measures can optionally be combined.

The reduction in gene expression can take place by suitable culturing, by genetic modification (mutation) of the signal structures of gene expression or also by the antisense-RNA technique. Signal structures of gene expression are, for example, repressor genes, activator genes, operators, promoters, attenuators, ribosome binding sites, the start codon and terminators. The expert can find information in this respect, inter alia, for example, in Jensen and Hammer (Biotechnology and Bioengineering 58: 191–195 (1998)), in Carrier and Keasling (Biotechnology Progress 15: 58–64 (1999)), Franch and Gerdes (Current Opinion in Microbiology 3: 159–164 (2000)) and in known textbooks of genetics and molecular biology, such as, for example, the textbook of Knippers ("Molekulare Genetik [Molecular Genetics]", 6th edition, Georg Thieme Verlag, Stuttgart, Germany, 1995) or that of Winnacker ("Gene und Klone [Genes and Clones]", VCH Verlagsgesellschaft, Weinheim, Germany, 1990).

Mutations which lead to a change or reduction in the catalytic properties of enzyme proteins are known from the prior art. Examples which may be mentioned are the works of Qiu and Goodman (Journal of Biological Chemistry 272: 8611–8617 (1997)), Yano et al. (Proceedings of the National Academy of Sciences, USA 95: 5511–5515 (1998)), Wente and Schachmann (Journal of Biological Chemistry 266: 20833–20839 (1991)). Summarizing descriptions can be found in known textbooks of genetics and molecular biology, such as e.g. that by Hagemann ("Allgemeine Genetik [General Genetics]", Gustav Fischer Verlag, Stuttgart, 1986).

Possible mutations are transitions, transversions, insertions and deletions. Depending on the effect of the amino acid exchange on the enzyme activity, "missense mutations" or nonsense mutations are referred to. Insertions or deletions of at least one base pair in a gene lead to "frame shift mutations", which lead to incorrect amino acids being incorporated or translation being interrupted prematurely. If a stop codon is formed in the coding region as a consequence of the mutation, this also leads to a premature termination of the translation. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik [Molecular Genetics]", 6th edition, Georg Thieme Verlag, Stuttgart, Germany, 1995), that by Winnacker ("Gene und Klone [Genes and Clones]", VCH Verlagsgesellschaft, Weinheim, Germany, 1990) or that by Hagemann ("Allgemeine Genetik [General Genetics]", Gustav Fischer Verlag, Stuttgart, 1986).

Suitable mutations in the genes, such as, for example, deletion mutations, can be incorporated into suitable strains by gene or allele replacement.

A conventional method is the method, described by Hamilton et al. (Journal of Bacteriology 171: 4617–4622 (1989)), of gene replacement with the aid of a conditionally replicating pSC101 derivative pMAK705. Other methods described in the prior art, such as, for example, those of Martinez-Morales et al. (Journal of Bacteriology 181: 1999, 7143–7148 (1999)) or those of Boyd et al. (Journal of Bacteriology 182: 842–847 (2000)), can likewise be used.

It is also possible to transfer mutations in the particular genes or mutations which affect expression of the particular genes into various strains by conjugation or transduction.

It may furthermore be advantageous for the production of L-amino acids, in particular L-threonine, with strains of the Enterobacteriaceae family, in addition to attenuation of the aspA gene, for one or more enzymes of the known threonine biosynthesis pathway or enzymes of anaplerotic metabolism or enzymes for the production of reduced nicotinamide adenine dinucleotide phosphate or enzymes of glycolysis or PTS enzymes or enzymes of sulfur metabolism to be enhanced.

The term "enhancement" in this connection describes the increase in the intracellular activity of one or more enzymes or proteins in a microorganism which are coded by the corresponding DNA, for example by increasing the number of copies of the gene or genes, using a potent promoter or a gene which codes for a corresponding enzyme or protein with a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

Thus, for example, at the same time one or more of the genes chosen from the group consisting of the thrABC operon which codes for aspartate kinase, homoserine dehydrogenase, homoserine kinase and threonine synthase (U.S. Pat. No. 4,278,765), the pyc gene of Corynebacterium glutamicum which codes for pyruvate carboxylase (WO 99/18228), the pps gene which codes for phosphoenol pyruvate synthase (Molecular and General Genetics 231(2): 332–336 (1992)), the ppc gene which codes for phosphoenol pyruvate carboxylase (Gene 31: 279–283 (1984)), the pntA and pntB genes which code for transhydrogenase (European Journal of Biochemistry 158: 647–653(1986)), the rhtB gene which imparts homoserine resistance (EP-A-0 994 190), the mqo gene which codes for malate:quinone oxidoreductase (WO 02/06459), the rhtC gene which imparts threonine resistance (EP-A-1 013 765), the thrE gene of Corynebacterium glutamicum which codes for the threonine export protein (WO 01/92545), the gdhA gene which codes for glutamate dehydrogenase (Nucleic Acids Research 11: 5257–5266 (1983); Gene 23: 199–209 (1983)), the hns gene which codes for the DNA-binding protein HLP-II (Molecular and General Genetics 212: 199–202 (1988)), the pgm gene which codes for phosphoglucomutase (Journal of Bacteriology 176: 5847–5851 (1994)), the fba gene which codes for fructose biphosphate aldolase (Biochemical Journal 257: 529–534 (1989)), the ptsH gene of the ptsHIcrr operon which codes for the phosphohistidine protein hexose phosphotransferase of the phosphotransferase system PTS (Journal of Biological Chemistry 262: 16241–16253 (1987)), the ptsI gene of the ptsHIcrr operon which codes for enzyme I of the phosphotransferase system PTS (Journal of Biological Chemistry 262: 16241–16253 (1987)), the crr gene of the ptsHIcrr operon which codes for the glucose-specific IIA component of the phosphotransferase system PTS (Journal of Biological Chemistry 262: 16241–16253 (1987)), the ptsG gene which codes for the glucose-specific IIBC component (Journal of Biological Chemistry 261: 16398–16403 (1986)), the lrp gene which codes for the regulator of the leucine regulon (Journal of Biological Chemistry 266: 10768–10774 (1991)), the mopB gene which codes for 10 Kd chaperone (Journal of Biological Chemistry 261: 12414–12419 (1986)) and is also known by the name groES, the ahpC gene of the ahpCF operon which codes for the small sub-unit of alkyl hydroperoxide reductase (Proceedings of the National Academy of Sciences of the United States of America 92: 7617–7621 (1995)), the ahpF gene of the ahpCF operon which codes for the large sub-unit of alkyl hydroperoxide reductase (Proceedings of the National Academy of Sciences USA 92: 7617–7621 (1995)), the cysK gene which codes for cysteine synthase A (Journal of Bacteriology 170: 3150–3157 (1988)), the cysB gene which codes for the regulator of the cys regulon (Journal of Biological Chemistry 262: 5999–6005 (1987)), the cysJ gene of the cysJIH operon which codes for the flavoprotein of NADPH sulfite reductase (Journal of Biological Chemistry 264: 15796–15808 (1989), Journal of Biological Chemistry 264: 15726–15737 (1989)), the cysI gene of the cysJIH operon which codes for the haemoprotein of NADPH sulfite reductase (Journal of Biological Chemistry 264: 15796–15808 (1989), Journal of Biological Chemistry 264: 15726–15737 (1989)) and the cysH gene of the cysJIH operon which codes for adenylyl sulfate reductase (Journal of Biological Chemistry 264: 15796–15808 (1989), Journal of Biological Chemistry 264: 15726–15737 (1989))

can be enhanced, in particular over-expressed.

The use of endogenous genes is in general preferred. "Endogenous genes" or "endogenous nucleotide sequences" are understood as meaning the genes or nucleotide sequences present in the population of a species.

It may furthermore be advantageous for the production of L-amino acids, in particular L-threonine, in addition to attenuation of the aspA gene, for one or more of the genes chosen from the group consisting of the tdh gene which codes for threonine dehydrogenase (Journal of Bacteriology 169: 4716–4721 (1987)), the mdh gene which codes for malate dehydrogenase (E.C. 1.1.1.37) (Archives in Microbiology 149: 36–42 (1987)), the gene product of the open reading frame (orf) yjfA (Accession Number AAC77180 of the National Center for Biotechnology Information (NCBI, Bethesda, Md., USA)), the gene product of the open reading frame (orf) ytfP (Accession Number AAC77179 of the National Center for Biotechnology Information (NCBI, Bethesda, Md., USA)), the pckA gene which codes for the enzyme phosphoenol pyruvate carboxykinase (Journal of Bacteriology 172: 7151–7156 (1990)), the poxB gene which codes for pyruvate oxidase (Nucleic Acids Research 14(13): 5449–5460 (1986)), the aceA gene which codes for the enzyme isocitrate lyase (Journal of Bacteriology 170: 4528–4536 (1988)), the dgsA gene which codes for the DgsA regulator of the phosphotransferase system (Bioscience, Biotechnology and Biochemistry 59: 256–261 (1995)) and is also known under the name of the mlc gene, the fruR gene which codes for the fructose repressor (Molecular and General Genetics 226: 332–336 (1991)) and is also known under the name of the cra gene, the rpos gene which codes for the sigma$^{38}$ factor (WO 01/05939) and is also known under the name of the katF gene, the aceB gene which codes for malate synthase A (Nucleic Acids Research 16(19.): 9342 (1988), the aceK gene which codes for isocitrate dehydrogenase kinase/phosphatase (Journal of Bacteriology 170(1): 89–97 (1988)) and the ugpB gene which codes for the periplasmic binding protein of the sn-glycerol 3-phosphate transport system (Molecular Microbiology 2(6): 767–775 (1988))

to be attenuated, in particular eliminated or for the expression thereof to be reduced.

It may furthermore be advantageous for the production of L-amino acids, in particular L-threonine, in addition to attenuation of the aspA gene, to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention can be cultured in the batch process (batch culture), the fed batch process (feed process) or the repeated fed batch process (repetitive feed process). A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and optionally cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 25° C. to 45° C., and preferably 30° C. to 40° C. Culturing is continued until a maximum of L-amino acids or L-threonine has formed. This target is usually reached within 10 hours to 160 hours.

The analysis of L-amino acids can be carried out by anion exchange chromatography with subsequent ninhydrin derivation, as described by Spackman et al. (Analytical Chemistry 30: 1190–1206 (1958)), or it can take place by reversed phase HPLC as described by Lindroth et al. (Analytical Chemistry 51: 1167–1174 (1979)).

The process according to the invention is used for the fermentative preparation of L-amino acids, such as, for example, L-threonine, L-isoleucine, L-valine, L-methionine, L-homoserine and L-lysine, in particular L-threonine.

A pure culture of the *Escherichia coli* K-12 strain DH5α/pMAK705 was deposited as DSM 13720 on 8Sep. 2000 at the Deutsche Sammlung für Mikroorganismen und Zellkulturen (DSMZ=German Collection of Microorganisms and Cell Cultures, Braunschweig, Germany) in accordance with the Budapest Treaty.

The present invention is explained in more detail in the following with the aid of embodiment examples.

The isolation of plasmid DNA from *Escherichia coli* and all techniques of restriction, ligation, Klenow and alkaline phosphatase treatment are carried out by the method of Sambrook et al. (Molecular Cloning—A Laboratory Manual (1989) Cold Spring Harbor Laboratory Press). Unless described otherwise, the transformation of *Escherichia coli* is carried out by the method of Chung et al. (Proceedings of the National Academy of Sciences of the United States of America 86: 2172–2175 (1989)).

The incubation temperature for the preparation of strains and transformants is 37° C. Temperatures of 30° C. and 44° C. are used in the gene replacement method of Hamilton et al.

EXAMPLE 1

Construction of the Deletion Mutation of the aspA Gene.

Parts of the gene regions lying upstream and downstream of the aspA gene and parts of the 5' and 3' region of the aspA gene are amplified from *Escherichia coli* K12 using the polymerase chain reaction (PCR) and synthetic oligonucleotides. Starting from the nucleotide sequence of the aspA gene and sequences lying upstream and downstream in *E. coli* K12 MG1655 (SEQ ID No. 1, Accession Number AE000486 and AE000487), the following PCR primers are synthesized (MWG Biotech, Ebersberg, Germany):

```
aspA5'-1:  5'-GCTGCATCAGCACGAAATTC-3'  (SEQ ID No. 3)

aspA5'-2:  5'-CCATTACCATACCGCGAACA-3'  (SEQ ID No. 4)

aspA3'-1:  5'-TGGCAGCAGAAGCAGGTCAG-3'  (SEQ ID No. 5)

aspA3'-2:  5'-TAGTCCAGACCGCCAGCAAC-3'  (SEQ ID No. 6)
```

The chromosomal *E. coli* K12 MG1655 DNA employed for the PCR is isolated according to the manufacturer's instructions with "Qiagen Genomic-tips 100/G" (QIAGEN, Hilden, Germany). A DNA fragment approx. 650 bp in size from the 5' region of the aspA gene region (called aspA5') and a DNA fragment approx. 700 bp in size from the 3' region of the aspA gene region (called aspA3') can be amplified with the specific primers under standard PCR conditions (Innis et al. (1990) PCR Protocols. A Guide to Methods and Applications, Academic Press) with Taq-DNA polymerase (Gibco-BRL, Eggenstein, Germany). The PCR products are each ligated with the vector pCR2.1-TOPO (TOPO TA Cloning Kit, Invitrogen, Groningen, The Netherlands) in accordance with the manufacturer's instructions and transformed into the E. coli strain TOP10F'. Selection of plasmid-carrying cells takes place on LB agar, to which 50 µg/ml ampicillin are added. After isolation of the plasmid DNA, the vector pCR2.1-TOPOaspA3' is cleaved with the restriction enzymes XbaI and Ecl136II. The aspA3' fragment is isolated after separation in 0.8% agarose gel with the aid of the QIAquick Gel Extraction Kit (QIAGEN, Hilden, Germany). After isolation of the plasmid DNA the vector pCR2.1-TOPOaspA5' is cleaved with the enzymes EcoRV and XbaI and ligated with the aspA3' fragment isolated. The E. coli strain DH5α is transformed with the ligation batch and plasmid-carrying cells are selected on LB agar, to which 50 µg/ml ampicillin are added. After isolation of the plasmid DNA those plasmid in which the mutagenic DNA sequence shown in SEQ ID No. 7 is cloned are detected by control cleavage with the enzymes EcoRI, XbaI and HindIII. One of the plasmids is called pCR2.1-TOPOΔaspA (=pCR2.1-TOPOdeltaaspA).

EXAMPLE 2

Construction of the Replacement Vector pMAK705ΔaspA

The ΔaspA allele described in example 1 is isolated from the vector pCR2.1-TOPOΔaspA after restriction with the enzymes HindIII and XbaI and separation in 0.8% agarose gel, and ligated with the plasmid pMAK705 (Hamilton et al., Journal of Bacteriology 171: 4617–4622 (1989)), which has been digested with the enzymes HindIII and XbaI. The ligation batch is transformed in DH5α and plasmid-carrying cells are selected on LB agar, to which 20 µg/ml chloramphenicol are added. Successful cloning is demonstrated after isolation of the plasmid DNA and cleavage with the enzymes HindIII and XbaI. The replacement vector formed, pMAK705ΔaspA (=pMAR705deltaaspA), is shown in FIG. 1.

EXAMPLE 3

Position-Specific Mutagenesis of the aspA Gene in the E. coli Strain MG442

The L-threonine-producing E. coli strain MG442 is described in the patent specification U.S. Pat. No. 4,278,765 and deposited as CMIM B-1628 at the Russian National Collection for Industrial Microorganisms (VKPM, Moscow, Russia).

For replacement of the chromosomal aspA gene with the plasmid-coded deletion construct, MG442 is transformed with the plasmid pMAK705ΔaspA. The gene replacement is carried out using the selection method described by Hamilton et al. (Journal of Bacteriology 171: 4617–4622 (1989)) and is verified by standard PCR methods (Innis et al. (1990) PCR Protocols. A Guide to Methods and Applications, Academic Press) with the following oligonucleotide primers:

aspA5'-1: 5'-GCTGCATCAGCACGAAATTC-3' (SEQ ID No. 3)

aspA3'-2: 5'-TAGTCCAGACCGCCAGCAAC-3' (SEQ ID No. 6)

After replacement has taken place, MG442 contains the form of the ΔaspA allele shown in SEQ ID No. 8. The strain obtained is called MG442ΔaspA.

EXAMPLE 4

Preparation of L-threonine with the Strain MG442ΔaspA

MG442ΔaspA is multiplied on minimal medium with the following composition: 3.5 g/l $Na_2HPO_4*2H_2O$, 1.5 g/l $KH_2PO_4$, 1 g/l $NH_4Cl$, 0.1 g/l $MgSO_4*7H_2O$, 2 g/l glucose, 20 g/l agar. The formation of L-threonine is checked in batch cultures of 10 ml contained in 100 ml conical flasks. For this, 10 ml of preculture medium of the following composition: 2 g/l yeast extract, 10 g/l $(NH_4)_2SO_4$, 1 g/l $KH_2PO_4$, 0.5 g/l $MgSO_4*7H_2O$, 15 g/l $CaCO_3$, 20 g/l glucose are inoculated and the batch is incubated for 16 hours at 37° C. and 180 rpm on an ESR incubator from Kuhner AG (Birsfelden, Switzerland). 250 µl of this preculture are transinoculated into 10 ml of production medium (25 g/l $(NH_4)_2SO_4$, 2 g/l $KH_2PO_4$, 1 g/l $MgSO_4*7H_2O$, 0.03 g/l $FeSO_4*7H_2O$, 0.018 g/l $MnSO_4*1H_2O$, 30 g/l $CaCO_3$, 20 g/l glucose) and the batch is incubated for 48 hours at 37° C. After the incubation the optical density. (OD) of the culture suspension is determined with an LP2W photometer from Dr. Lange (Düsseldorf, Germany) at a measurement wavelength of 660 nm.

The concentration of L-threonine formed is then determined in the sterile-filtered culture supernatant with an amino acid analyzer from Eppendorf-BioTronik (Hamburg, Germany) by ion exchange chromatography and post-column reaction with ninhydrin detection.

The result of the experiment is shown in Table 1.

TABLE 1

| Strain | OD (660 nm) | L-Threonine g/l |
|---|---|---|
| MG442 | 6.0 | 1.5 |
| MG442ΔaspA | 5.5 | 1.9 |

Figure 1:
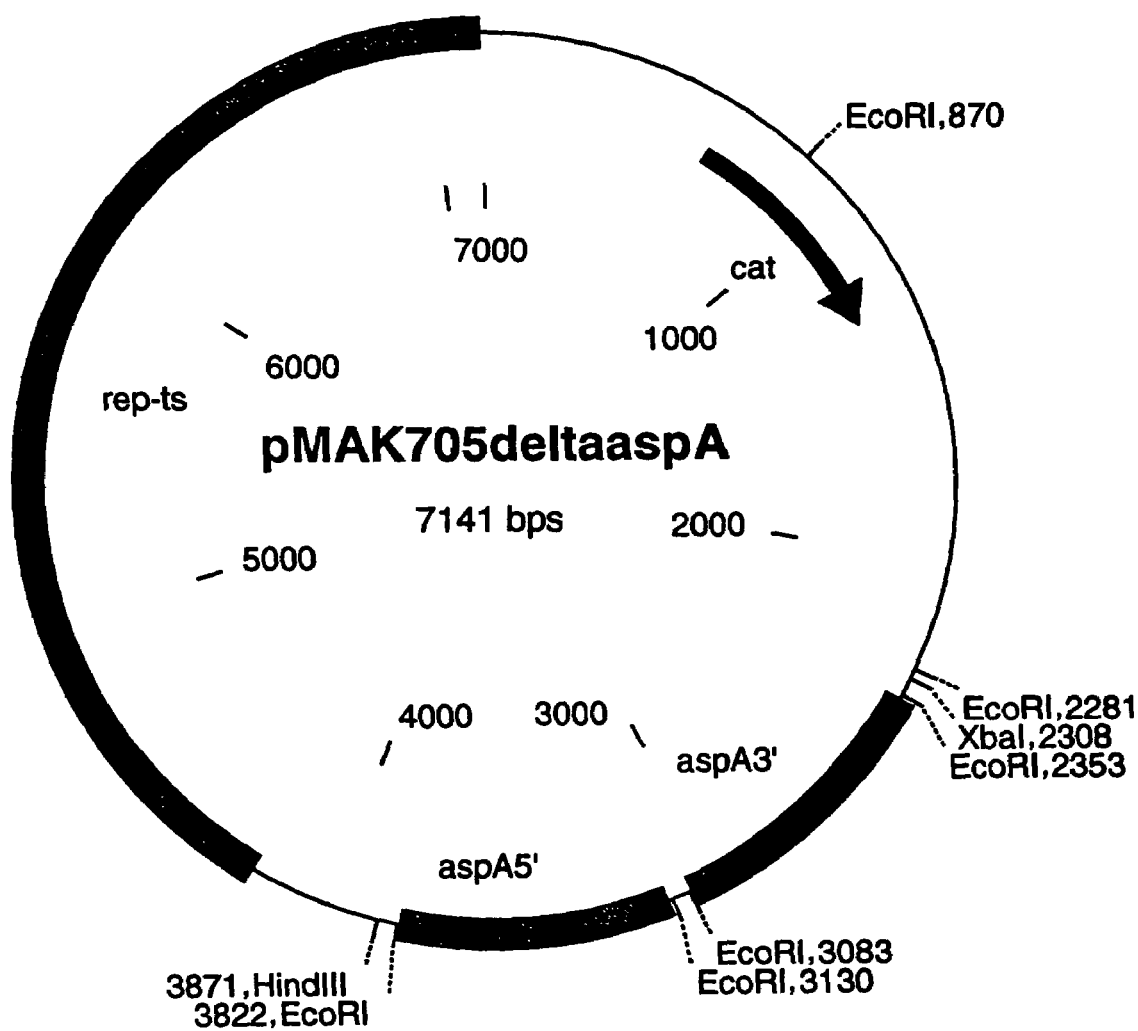
FIG. 1: pMAK705ΔaspA (=pMAK705deltaaspA)

The length data are to be understood as approx. data. The abbreviations and designations used have the following meaning:

cat: Chloramphenicol resistance gene rep-ts: Temperature-sensitive replication region of the plasmid pSC101 aspA5': Part of the 5' region of the aspA gene and the region lying upstream aspA3': Part of the 3' region of the aspA gene and the region lying downstream The abbreviations for the restriction enzymes have the following meaning EcoRI: Restriction endonuclease from Escherichia coli HindIII: Restriction endonuclease from Haemophilus influenza xbaI: Restriction endonuclease from Xanthomonas badrii

What is claimed is:

1. A process for the preparation of an L-amino acid selected from the group consisting of L-lysine, L-valine, L-homoserine and L-threonine, comprising: culturing a recombinant microorganism of the genus *Escherichia* for a time and under conditions suitable for the production of said L-amino acid, wherein: said recombinant microorganism has a deletion or mutation of the gene encoding aspartate animonium lyase (aspA) and having the amino acid sequence of SEQ ID NO:2; and wherein said deletion or mutation results in the elimination of aspA enzymatic activity in said microorganism.

2. The process of claim 1, wherein said L-amino acid is L-lysine.

3. The process of claim 1, wherein said L-amino acid is L-valine.

4. The process of claim 1, wherein said L-amino acid is L-homosenne.

5. The process of claim 1, wherein said L-amino acid is L-threonine.

6. The process of any one of claims 2–5, wherein said gene is deleted or mutated by one or more methods selected from the group consisting of:
   a) deletion mutagenesis with deletion of at least one base pair in said gene encoding aspartate ammonium lyase (aspA);
   b) insertional mutagenesis due to homologous recombination; and
   c) transition or transversion mutagenesis with incorporation of a nonsense mutation into said gene encoding aspartate ammonium lyase (aspA).

7. The process of any one of claims 2–5, further comprising:
   a) allowing said L-amino acid to become concentrated in said medium or in the cells of said recombinant microorganism; and
   b) after step a), isolating said L-amino acid along with 0–100% of the biomass or other constituents in said medium.

8. The process of claim 6, further comprising:
   a) allowing said L-amino acid to become concentrated in said medium or in the cells of said recombinant microorganism; and
   b) after step a), isolating said L-amino acid along with 0–100% of the biomass or other constituents in said medium.

9. The process of claim 1, wherein:
   a) said L-amino acid is L-lysine or L-threonine;
   b) said gene is deleted or mutated by insertional mutagenesis due to homologous recombination; and
   c) said process further comprises:
      i) allowing said L-amino acid to become concentrated in said medium or in the cells of said recombinant microorganism; and
      ii) after step i), isolating said L-amino acid along with 0–100% of the biomass or other constituents in said medium.

10. The process of claim 7, wherein said recombinant microorganism overexpresses one or more gene(s) selected from the group consisting of:
   a) the *E. coli* thrABC operon which codes for aspartate kinase, homoserine dehydrogenase, homoserine kinase and threonine synthase;
   b) the *C. glutamicum* pyc gene which codes for pyruvate carboxylase;
   c) the *E. coli* pps gene which codes for phosphoenol pyruvate synthase;
   d) the *E. coli* ppc gene which codes for phosphoenol pyruvate carboxylase;
   e) the *E. coli* pntA and pntB genes which code for transhydrogenase;
   f) the *E. cloi* rhtB gene which imparts homoserine resistance;
   g) the *E. coli* mqo gene which codes for malate:quinone oxidoreductase;
   h) the *E. coli* rhtC gene which imparts threonine resistance;
   i) the *C. glutamicum* thrE gene which codes for the threonine export protein;
   j) the *E. coli* gdhA gene which codes for glutamate dehydrogenase;
   k) the *E. coli* hns gene which codes for the DNA-binding protein HLP-II;
   l) the *E. coli* pgm gene which codes for phosphoglucomutase;
   m) the *E. coli* fba gene which codes for fructose biphosphate aldolase;
   n) the *E. coli* ptsH gene which codes for the phosphohistidine protein hexose phosphotransferase;
   o) the *E. coli* ptsI gene which codes for enzyme I of the phosphotransferase system;
   p) the *E. coli* crr gene which codes for the glucose-specific IIA component;
   q) the *E. coli* ptsG gene which codes for the glucose-specific IIBC component;
   r) the *E. coli* lrp gene which codes for the regulator of the leucine regulon;
   s) the *E. coli* mopB gene which codes for 10 Kd chaperone;
   t) the *E. coli* ahpC gene which codes for the small sub-unit of alkyl hydroperoxide reductase;
   u) the *E. coli* ahpF gene which codes for the large sub-unit of alkyl hydroperoxide reductase;
   v) the *E. coli* cysK gene which codes for cysteine synthase A;
   w) the *E. coli* cysB gene which codes for the regulator of the cys regulon;
   x) the *E. coli* cysJ gene which codes for the flavoprotein of NADPH sulfite reductase;
   y) the *E. coli* cysI gene which codes for the haemoprotein of NADPH sulfite reductase; and
   z) the *E. coli* cysH gene which codes for adenylyl sulfate reductase.

11. The process of claim 7, wherein one or more *E. coli* gene(s) are deleted in said microorganism, said one or more genes being selected from the group consisting of:
   a) the tdh gene which codes for threonine dehydrogenase;
   b) the mdh gene which codes for malate dehydrogenase;
   c) the gene product of the open reading frame (orf) yjfA;
   d) the gene product of the open reading frame (orf) ytfP;
   e) the pckA gene which codes for phosphoenol pyruvate carboxykinase;
   f) the poxB gene which codes for pyruvate oxidase;
   g) the aceA gene which codes for isocitrate lyase;
   h) the dgsA gene which codes for the DgsA regulator of the phosphotransferase system;
   i) the fruR gene which codes for the fructose repressor;
   j) the rpoS gene which codes for the sigma$^{38}$ factor;
   k) the aceB gene which codes for malate synthase A;
   l) the aceK gene which codes for isocitrate dehydrogenase kinase/phosphatase; and
   m) the ugpB gene which codes for the periplasmic binding protein of the sn-glycerol 3-phosphate transport system.

* * * * *

SEQUENCE LISTING

<160> NUMBER OF SEQ ID NOS: 8

<210> SEQ ID NO 1
<211> LENGTH: 2280
<212> TYPE: DNA
<213> ORGANISM: Escherichia coli
<220> FEATURE:
<221> NAME/KEY: CDS
<222> LOCATION: (470)..(1951)
<223> OTHER INFORMATION: aspA gene

<400> SEQUENCE: 1

```
gctgcatcag cacgaaattc ttaaagccct ggttacgtac cagtgacata ccgataactg      60
acgtgaatat aaccagcacg agggtcagca ataccoccaa tacatgggca acctgaataa     120
agattgaaat ctcaatatag acataaagga aaatggcaat aaaaggtaac cagcgcaaag     180
gtttctcctg taatagcagc cggttaaccc cggctacctg aatgggttgc gaatcgcgtt     240
tagcttatat tgtggtcatt agcaaaattt caagatgttt gcgcaactat ttttggtagt     300
aatcccaaag cggtgatcta tttcacaaat taataattaa ggggtaaaaa ccgacactta     360
aagtgatcca gattacggta gaaatcctca agcagcatat gatctcgggt attcggtcga     420 tgcagggat aatcgtcggt cgaaaaacat tcgaaaccac atatattct gtg tgt tta      478
                                                    Met Cys Leu
                                                     1 aag caa atc att ggc agc ttg aaa aag aag gtt cac atg tca aac aac        526
Lys Gln Ile Ile Gly Ser Leu Lys Lys Lys Val His Met Ser Asn Asn
  5               10                  15 att cgt atc gaa gaa gat ctg ttg ggt acc agg gaa gtt cca gct gat        574
Ile Arg Ile Glu Glu Asp Leu Leu Gly Thr Arg Glu Val Pro Ala Asp
 20                  25                  30                  35 gcc tac tat ggt gtt cac act ctg aga gcg att gaa aac ttc tat atc        622
Ala Tyr Tyr Gly Val His Thr Leu Arg Ala Ile Glu Asn Phe Tyr Ile
                 40                  45                  50 agc aac aac aaa atc agt gat att cct gaa ttt gtt cgc ggt atg gta        670
Ser Asn Asn Lys Ile Ser Asp Ile Pro Glu Phe Val Arg Gly Met Val
             55                  60                  65 atg gtt aaa aaa gcc gca gct atg gca aac aaa gag ctg caa acc att        718
Met Val Lys Lys Ala Ala Ala Met Ala Asn Lys Glu Leu Gln Thr Ile
         70                  75                  80 cct aaa agt gta gcg aat gcc atc att gcc gca tgt gat gaa gtc ctg        766
Pro Lys Ser Val Ala Asn Ala Ile Ile Ala Ala Cys Asp Glu Val Leu
     85                  90                  95 aac aac gga aaa tgc atg gat cag ttc ccg gta gac gtc tac cag ggc        814
Asn Asn Gly Lys Cys Met Asp Gln Phe Pro Val Asp Val Tyr Gln Gly
100                 105                 110                 115 ggc gca ggt act tcc gta aac atg aac acc aac gaa gtg ctg gcc aat        862
Gly Ala Gly Thr Ser Val Asn Met Asn Thr Asn Glu Val Leu Ala Asn
                120                 125                 130 atc ggt ctg gaa ctg atg ggt cac caa aaa ggt gaa tat cag tac ctg        910
Ile Gly Leu Glu Leu Met Gly His Gln Lys Gly Glu Tyr Gln Tyr Leu
            135                 140                 145 aac ccg aac gac cat gtt aac aaa tgt cag tcc act aac gac gcc tac        958
Asn Pro Asn Asp His Val Asn Lys Cys Gln Ser Thr Asn Asp Ala Tyr
        150                 155                 160 ccg acc ggt ttc cgt atc gca gtt tac tct tcc ctg att aag ctg gta       1006
Pro Thr Gly Phe Arg Ile Ala Val Tyr Ser Ser Leu Ile Lys Leu Val
    165                 170                 175
```

-continued

```
gat gcg att aac caa ctg cgt gaa ggc ttt gaa cgt aaa gct gtc gaa    1054
Asp Ala Ile Asn Gln Leu Arg Glu Gly Phe Glu Arg Lys Ala Val Glu
180             185                 190                 195 ttc cag gac atc ctg aaa atg ggt cgt acc cag ctg cag gac gca gta    1102
Phe Gln Asp Ile Leu Lys Met Gly Arg Thr Gln Leu Gln Asp Ala Val
                200                 205                 210 ccg atg acc ctc ggt cag gaa ttc cgc gct ttc agc atc ctg ctg aaa    1150
Pro Met Thr Leu Gly Gln Glu Phe Arg Ala Phe Ser Ile Leu Leu Lys
            215                 220                 225 gaa gaa gtg aaa aac atc caa cgt acc gct gaa ctg ctg ctg gaa gtt    1198
Glu Glu Val Lys Asn Ile Gln Arg Thr Ala Glu Leu Leu Leu Glu Val
        230                 235                 240 aac ctt ggt gca aca gca atc ggt act ggt ctg aac acg ccg aaa gag    1246
Asn Leu Gly Ala Thr Ala Ile Gly Thr Gly Leu Asn Thr Pro Lys Glu
    245                 250                 255 tac tct ccg ctg gca gtg aaa aaa ctg gct gaa gtt act ggc ttc cca    1294
Tyr Ser Pro Leu Ala Val Lys Lys Leu Ala Glu Val Thr Gly Phe Pro
260                 265                 270                 275 tgc gta ccg gct gaa gac ctg atc gaa gcg acc tct gac tgc ggc gct    1342
Cys Val Pro Ala Glu Asp Leu Ile Glu Ala Thr Ser Asp Cys Gly Ala
                280                 285                 290 tat gtt atg gtt cac ggc gcg ctg aaa cgc ctg gct gtg aag atg tcc    1390
Tyr Val Met Val His Gly Ala Leu Lys Arg Leu Ala Val Lys Met Ser
            295                 300                 305 aaa atc tgt aac gac ctg cgc ttg ctc tct tca ggc cca cgt gcc ggc    1438
Lys Ile Cys Asn Asp Leu Arg Leu Leu Ser Ser Gly Pro Arg Ala Gly
        310                 315                 320 ctg aac gag atc aac ctg ccg gaa ctg cag gcg ggc tct tcc atc atg    1486
Leu Asn Glu Ile Asn Leu Pro Glu Leu Gln Ala Gly Ser Ser Ile Met
    325                 330                 335 cca gct aaa gta aac ccg gtt gtt ccg gaa gtg gtt aac cag gta tgc    1534
Pro Ala Lys Val Asn Pro Val Val Pro Glu Val Val Asn Gln Val Cys
340                 345                 350                 355 ttc aaa gtc atc ggt aac gac acc act gtt acc atg gca gca gaa gca    1582
Phe Lys Val Ile Gly Asn Asp Thr Thr Val Thr Met Ala Ala Glu Ala
                360                 365                 370 ggt cag ctg cag ttg aac gtt atg gag ccg gtc att ggc cag gcc atg    1630
Gly Gln Leu Gln Leu Asn Val Met Glu Pro Val Ile Gly Gln Ala Met
            375                 380                 385 ttc gaa tcc gtt cac att ctg acc aac gct tgc tac aac ctg ctg gaa    1678
Phe Glu Ser Val His Ile Leu Thr Asn Ala Cys Tyr Asn Leu Leu Glu
        390                 395                 400 aaa tgc att aac ggc atc act gct aac aaa gaa gtg tgc gaa ggt tac    1726
Lys Cys Ile Asn Gly Ile Thr Ala Asn Lys Glu Val Cys Glu Gly Tyr
    405                 410                 415 gtt tac aac tct atc ggt atc gtt act tac ctg aac ccg ttc atc ggt    1774
Val Tyr Asn Ser Ile Gly Ile Val Thr Tyr Leu Asn Pro Phe Ile Gly
420                 425                 430                 435 cac cac aac ggt gac atc gtg ggt aaa atc tgt gcc gaa acc ggt aag    1822
His His Asn Gly Asp Ile Val Gly Lys Ile Cys Ala Glu Thr Gly Lys
                440                 445                 450 agt gta cgt gaa gtc gtt ctg gaa cgc ggt ctg ttg act gaa gcg gaa    1870
Ser Val Arg Glu Val Val Leu Glu Arg Gly Leu Leu Thr Glu Ala Glu
            455                 460                 465 ctt gac gat att ttc tcc gta cag aat ctg atg cac ccg gct tac aaa    1918
Leu Asp Asp Ile Phe Ser Val Gln Asn Leu Met His Pro Ala Tyr Lys
        470                 475                 480 gca aaa cgc tat act gat gaa agc gaa cag taa tcgtacaggg tagtacaaat    1971
Ala Lys Arg Tyr Thr Asp Glu Ser Glu Gln
    485                 490
```

-continued

```
aaaaaaggca cgtcagatga cgtgccttt ttcttgtgag cagtaactta aaataacaa        2031 tctaatatca acttgttaaa aaacaaggaa ggctaatatg ctagttgtag aactcatcat        2091
agttttgctg gcgatcttct tgggcgccag attgggggga ataggtattg gtttttgcagg      2151 cggattgggg gtgctggttc ttgccgctat tggcgttaaa cccggtaaca tcccgttcga      2211
tgtcatctcc attatcatgg cggttatcgc cgctatttct gccatgcagg ttgctggcgg      2271
tctggacta                                                              2280
```

<210> SEQ ID NO 2
<211> LENGTH: 493
<212> TYPE: PRT
<213> ORGANISM: Escherichia coli

<400> SEQUENCE: 2

```
Met Cys Leu Lys Gln Ile Ile Gly Ser Leu Lys Lys Val His Met
1               5                   10                  15

Ser Asn Asn Ile Arg Ile Glu Glu Asp Leu Leu Gly Thr Arg Glu Val
                20                  25                  30

Pro Ala Asp Ala Tyr Tyr Gly Val His Thr Leu Arg Ala Ile Glu Asn
            35                  40                  45

Phe Tyr Ile Ser Asn Asn Lys Ile Ser Asp Ile Pro Glu Phe Val Arg
        50                  55                  60

Gly Met Val Met Val Lys Ala Ala Met Ala Asn Lys Glu Leu
65                  70                  75                  80

Gln Thr Ile Pro Lys Ser Val Ala Asn Ala Ile Ala Ala Cys Asp
                85                  90                  95

Glu Val Leu Asn Asn Gly Lys Cys Met Asp Gln Phe Pro Val Asp Val
            100                 105                 110

Tyr Gln Gly Gly Ala Gly Thr Ser Val Asn Met Asn Thr Asn Glu Val
        115                 120                 125

Leu Ala Asn Ile Gly Leu Glu Leu Met Gly His Gln Lys Gly Glu Tyr
    130                 135                 140

Gln Tyr Leu Asn Pro Asn Asp His Val Asn Lys Cys Gln Ser Thr Asn
145                 150                 155                 160

Asp Ala Tyr Pro Thr Gly Phe Arg Ile Ala Val Tyr Ser Ser Leu Ile
                165                 170                 175

Lys Leu Val Asp Ala Ile Asn Gln Leu Arg Glu Gly Phe Glu Arg Lys
            180                 185                 190

Ala Val Glu Phe Gln Asp Ile Leu Lys Met Gly Arg Thr Gln Leu Gln
        195                 200                 205

Asp Ala Val Pro Met Thr Leu Gly Gln Glu Phe Arg Ala Phe Ser Ile
    210                 215                 220

Leu Leu Lys Glu Glu Val Lys Asn Ile Gln Arg Thr Ala Glu Leu Leu
225                 230                 235                 240

Leu Glu Val Asn Leu Gly Ala Thr Ala Ile Gly Thr Gly Leu Asn Thr
                245                 250                 255

Pro Lys Glu Tyr Ser Pro Leu Ala Val Lys Lys Leu Ala Glu Val Thr
            260                 265                 270

Gly Phe Pro Cys Val Pro Ala Glu Asp Leu Ile Glu Ala Thr Ser Asp
        275                 280                 285

Cys Gly Ala Tyr Val Met Val His Gly Ala Leu Lys Arg Leu Ala Val
    290                 295                 300

Lys Met Ser Lys Ile Cys Asn Asp Leu Arg Leu Leu Ser Ser Gly Pro
305                 310                 315                 320
```

-continued

Arg Ala Gly Leu Asn Glu Ile Asn Leu Pro Glu Leu Gln Ala Gly Ser
                325                 330                 335

Ser Ile Met Pro Ala Lys Val Asn Pro Val Val Pro Glu Val Val Asn
            340                 345                 350

Gln Val Cys Phe Lys Val Ile Gly Asn Asp Thr Thr Val Thr Met Ala
        355                 360                 365

Ala Glu Ala Gly Gln Leu Gln Leu Asn Val Met Glu Pro Val Ile Gly
370                 375                 380

Gln Met Phe Glu Ser Val His Ile Leu Thr Asn Ala Cys Tyr Asn
385                 390                 395                 400

Leu Leu Glu Lys Cys Ile Asn Gly Ile Thr Ala Asn Lys Glu Val Cys
                405                 410                 415

Glu Gly Tyr Val Tyr Asn Ser Ile Gly Ile Val Thr Tyr Leu Asn Pro
            420                 425                 430

Phe Ile Gly His His Asn Gly Asp Ile Val Gly Lys Ile Cys Ala Glu
        435                 440                 445

Thr Gly Lys Ser Val Arg Glu Val Val Leu Glu Arg Gly Leu Leu Thr
450                 455                 460

Glu Ala Glu Leu Asp Asp Ile Phe Ser Val Gln Asn Leu Met His Pro
465                 470                 475                 480

Ala Tyr Lys Ala Lys Arg Tyr Thr Asp Glu Ser Glu Gln
                485                 490

<210> SEQ ID NO 3
<211> LENGTH: 20
<212> TYPE: DNA
<213> ORGANISM: artificial sequence
<220> FEATURE:
<221> NAME/KEY: Primer
<222> LOCATION: (1)..(20)
<223> OTHER INFORMATION: aspA5 -1

<400> SEQUENCE: 3
gctgcatcag cacgaaattc                                            20

<210> SEQ ID NO 4
<211> LENGTH: 20
<212> TYPE: DNA
<213> ORGANISM: artificial sequence
<220> FEATURE:
<221> NAME/KEY: Primer
<222> LOCATION: (1)..(20)
<223> OTHER INFORMATION: aspA5 -2

<400> SEQUENCE: 4
ccattaccat accgcgaaca                                            20

<210> SEQ ID NO 5
<211> LENGTH: 20
<212> TYPE: DNA
<213> ORGANISM: artificial sequence
<220> FEATURE:
<221> NAME/KEY: Primer
<222> LOCATION: (1)..(20)
<223> OTHER INFORMATION: aspA3 -1

<400> SEQUENCE: 5
tggcagcaga agcaggtcag                                            20

<210> SEQ ID NO 6
<211> LENGTH: 20
<212> TYPE: DNA

-continued

```
<213> ORGANISM: artificial sequence
<220> FEATURE:
<221> NAME/KEY: Primer
<222> LOCATION: (1)..(20)
<223> OTHER INFORMATION: aspA3 -2

<400> SEQUENCE: 6
tagtccagac cgccagcaac                                                 20

<210> SEQ ID NO 7
<211> LENGTH: 1563
<212> TYPE: DNA
<213> ORGANISM: Escherichia coli
<220> FEATURE:
<221> NAME/KEY: misc_feature
<222> LOCATION: (1)..(1563)
<223> OTHER INFORMATION: mutagenic DNA
<220> FEATURE:
<221> NAME/KEY: misc_feature
<222> LOCATION: (1)..(60)
<223> OTHER INFORMATION: technical DNA / residues of polylinker
                        sequence
<220> FEATURE:
<221> NAME/KEY: misc_feature
<222> LOCATION: (61)..(734)
<223> OTHER INFORMATION: parts of the 5' region of the aspA gene
                        and regions lying upstream
<220> FEATURE:
<221> NAME/KEY: misc_feature
<222> LOCATION: (735)..(799)
<223> OTHER INFORMATION: technical DNA / residues of polylinker
                        sequence
<220> FEATURE:
<221> NAME/KEY: misc_feature
<222> LOCATION: (800)..(1511)
<223> OTHER INFORMATION: parts of the 3' region of the aspA gene
                        and regions lying downstream
<220> FEATURE:
<221> NAME/KEY: misc_feature
<222> LOCATION: (1512)..(1563)
<223> OTHER INFORMATION: technical DNA / residues of polylinker
                        sequence

<400> SEQUENCE: 7
agcttggtac cgagctcgga tccactagta acggccgcca gtgtgctgga attcgccctt      60
gctgcatcag cacgaaattc ttaaagccct ggttacgtac cagtgacata ccgataactg    120
acgtgaatat aaccagcacg agggtcagca ataccccaa tacatgggca acctgaataa    180
agattgaaat ctcaatatag acataaagga aaatggcaat aaaaggtaac cagcgcaaag    240
gtttctcctg taatagcagc cggttaaccc cggctacctg aatgggttgc gaatcgcgtt    300
tagcttatat tgtggtcatt agcaaaattt caagatgttt gcgcaactat ttttggtagt    360
aatcccaaag cggtgatcta tttcacaaat taataattaa ggggtaaaaa ccgacactta    420
aagtgatcca gattacggta gaaatcctca agcagcatat gatctcgggt attcggtcga    480
tgcaggggat aatcgtcggt cgaaaaacat tcgaaccac atatattctg tgtgtttaaa     540
gcaaatcatt ggcagcttga aaagaaggt tcacatgtca acaacattc gtatcgaaga     600 agatctgttg ggtaccaggg aagttccagc tgatgcctac tatggtgttc acactctgag    660
agcgattgaa aacttctata tcagcaacaa caaaatcagt gatattcctg aatttgttcg    720
cggtatggta atggaagggc gaattctgca gatctcggat ccactagtaa cggccgccag    780
tgtgctggaa ttcgcccttt ggcagcagaa gcaggtcagc tgcagttgaa cgttatggag    840
ccggtcattg gccaggccat gttcgaatcc gttcacattc tgaccaacgc ttgctacaac    900
ctgctggaaa aatgcattaa cggcatcact gctaacaaag aagtgtgcga aggttacgtt    960
```

```
tacaactcta tcggtatcgt tacttacctg aacccgttca tcggtcacca caacggtgac    1020
atcgtgggta aaatctgtgc cgaaaccggt aagagtgtac gtgaagtcgt tctggaacgc    1080
ggtctgttga ctgaagcgga acttgacgat attttctccg tacagaatct gatgcacccg    1140
gcttacaaag caaaacgcta tactgatgaa agcgaacagt aatcgtacag ggtagtacaa    1200
ataaaaaagg cacgtcagat gacgtgcctt ttttcttgtg agcagtaact taaaaataac    1260
aatctaatat caacttgtta aaaaacaagg aaggctaata tgctagttgt agaactcatc    1320
atagttttgc tggcgatctt cttgggcgcc agattggggg gaataggtat tggttttgca    1380
ggcggattgg gggtgctggt tcttgccgct attggcgtta aacccggtaa catcccgttc    1440
gatgtcatct ccattatcat ggcggttatc gccgctattt ctgccatgca ggttgctggc    1500
ggtctggact aaagggcgaa ttctgcagat atccatcaca ctggcggccg ctcgagcatg    1560
cat                                                                  1563
```

<210> SEQ ID NO 8
<211> LENGTH: 653
<212> TYPE: DNA
<213> ORGANISM: Escherichia coli
<220> FEATURE:
<221> NAME/KEY: misc_feature
<222> LOCATION: (1)..(653)
<223> OTHER INFORMATION: mutagenic DNA
<220> FEATURE:
<221> NAME/KEY: misc_feature
<222> LOCATION: (1)..(3)
<223> OTHER INFORMATION: start codon of the deltaaspA allele
<220> FEATURE:
<221> NAME/KEY: misc_feature
<222> LOCATION: (1)..(205)
<223> OTHER INFORMATION: 5' region of the deltaaspA allele
<220> FEATURE:
<221> NAME/KEY: misc_feature
<222> LOCATION: (206)..(270)
<223> OTHER INFORMATION: technical DNA / residues of the polylinker
                        sequence
<220> FEATURE:
<221> NAME/KEY: misc_feature
<222> LOCATION: (271)..(653)
<223> OTHER INFORMATION: 3' region of the deltaaspA allele
<220> FEATURE:
<221> NAME/KEY: misc_feature
<222> LOCATION: (651)..(653)
<223> OTHER INFORMATION: stop codon of the deltaaspA allele

<400> SEQUENCE: 8

```
gtgtgtttaa agcaaatcat tggcagcttg aaaaagaagg ttcacatgtc aaacaacatt     60
cgtatcgaag aagatctgtt gggtaccagg gaagttccag ctgatgccta ctatggtgtt    120
cacactctga gagcgattga aaacttctat atcagcaaca acaaaatcag tgatattcct    180
gaatttgttc gcggtatggt aatggaaggg cgaattctgc agatctcgga tccactagta    240
acggccgcca gtgtgctgga attcgccctt tggcagcaga agcaggtcag ctgcagttga    300
acgttatgga gccggtcatt ggccaggcca tgttcgaatc cgttcacatt ctgaccaacg    360
cttgctacaa cctgctggaa aaatgcatta acggcatcac tgctaacaaa gaagtgtgcg    420
aaggttacgt ttacaactct atcggtatcg ttacttacct gaacccgttc atcggtcacc    480
acaacggtga catcgtgggt aaaatctgtg ccgaaaccgg taagagtgta cgtgaagtcg    540
ttctggaacg cggtctgttg actgaagcgg aacttgacga tattttctcc gtacagaatc    600
tgatgcaccc ggcttacaaa gcaaaacgct atactgatga agcgaacagt taa           653
```